United States Patent
Wenger et al.

(10) Patent No.: US 12,129,304 B2
(45) Date of Patent: Oct. 29, 2024

(54) TREATMENT OF CD20-POSITIVE B-CELL LYMPHOMA WITH OBINUTUZUMAB

(71) Applicant: F. Hoffmann-La Roche AG, Basel (CH)

(72) Inventors: Michael Wenger, Basel (CH); Mehrdad Mobasher, South San Francisco, CA (US); Chin-Yu Lin, South San Francisco, CA (US)

(73) Assignee: F. Hoffmann-La Roche AG, Basel (CH)

( * ) Notice: Subject to any disclaimer, the term of this patent is extended or adjusted under 35 U.S.C. 154(b) by 315 days.

(21) Appl. No.: 16/756,057

(22) PCT Filed: Oct. 19, 2018

(86) PCT No.: PCT/JP2018/038924
§ 371 (c)(1),
(2) Date: Apr. 14, 2020

(87) PCT Pub. No.: WO2019/017499
PCT Pub. Date: Jan. 24, 2019

(65) Prior Publication Data
US 2020/0299398 A1    Sep. 24, 2020

Related U.S. Application Data

(60) Provisional application No. 62/574,297, filed on Oct. 19, 2017.

(51) Int. Cl.
| | |
|---|---|
| *C07K 16/28* | (2006.01) |
| *A61K 39/00* | (2006.01) |
| *A61K 45/06* | (2006.01) |
| *A61K 47/10* | (2017.01) |
| *A61K 47/18* | (2017.01) |
| *A61P 35/00* | (2006.01) |

(52) U.S. Cl.
CPC .......... *C07K 16/2887* (2013.01); *A61K 47/10* (2013.01); *A61K 47/183* (2013.01); *A61P 35/00* (2018.01); *A61K 2039/505* (2013.01); *A61K 2039/545* (2013.01); *A61K 45/06* (2013.01)

(58) Field of Classification Search
CPC .......... C07K 16/2887; C07K 2317/732; A61K 47/10; A61K 47/183; A61K 45/06; A61K 2039/505; A61K 2039/545; A61P 35/00
See application file for complete search history.

(56) References Cited

U.S. PATENT DOCUMENTS

2020/0002400 A1    1/2020    Yao et al.

FOREIGN PATENT DOCUMENTS

| CN | 108395482 B | 2/2021 | |
|---|---|---|---|
| JP | 2011-506538 A | 3/2011 | |
| WO | WO-2005/044859 A2 | 5/2005 | |
| WO | WO-2009/080541 A1 | 7/2009 | |
| WO | WO-2016/024228 A1 | 2/2016 | |
| WO | WO-2017100722 A1 * | 6/2017 | ............. A61P 13/12 |
| WO | WO-2019/017449 A1 | 1/2019 | |

OTHER PUBLICATIONS

National Cancer Institute, Definition of B-cell lymphoma, accessed Dec. 21, 2021 (Year: 2021).*
Tobinai K, Klein C, Oya N, Fingerle-Rowson G. A Review of Obinutuzumab (GA101), a Novel Type II Anti-CD20 Monoclonal Antibody, for the Treatment of Patients with B-Cell Malignancies. Adv Ther. Feb. 2017;34(2):324-356. doi: 10.1007/s12325-016-0451-1. Epub Dec. 21, 2016. (Year: 2021).*
Tsujimura et al., Blood, vol. 128, Issue 22, 2016, p. 5389, (Year: 2016).*
FDA, Highlights of Prescribing Information (Gayzva), 2014 (Year: 2014).*
Storfjell et al. (JONA 38(5):244-249. (2008) (Year: 2008).*
Carayon et al. (Chapt. 30 of Patient Safety and Quality. 203-216. (2008) (Year: 2008).*
Peipins et al. (BMC Public Health. 12(520):1-9. (2012) (Year: 2012).*
Obinutuzumab Label (2016) (Year: 2016).*
"Highlights of Prescribing Information (Gazyva®)," FDA, <https://www.accessdata.fda.gov/drugsatfda_docs/label/2022/125486s029lbl.pdf>, dated Feb. 2022 (32 pages).
Cartron et al. "Obinutuzumab (GA101) in relapsed/refractory chronic lymphocytic leukemia: final data from the phase 1/2 GAUGUIN study," Blood. vol. 124(14):2196-2202 (2014).
Herter et al. "Preclinical Activity of the Type II CD20 Antibody GA101 (Obinutuzumab) Compared with Rituximab and Ofatumumab In Vitro and in Xenograft Models," Mol Cancer Ther. vol. 12(10):2031-2042 (2013).
Hiddeman et al."Immunochemotherapy With Obinutuzumab or Rituximab in Previously Untreated Follicular Lymphoma in the Randomised Phase III Gallium Study: Analysis By Chemotherapy Regimen," Hermatol Oncol. vol. 35: 117-119 (2017).
Marcus et al. "Obinutuzumab for the First-Line Treatment of Follicular Lymphoma," N Engl J Med. vol. 337: 1331-1344 (2017).
Mossner et al. "Increasing the efi¬ cacy of CD20 antibody therapy through the engineering of a new type II anti-CD20 antibody with enhanced direct and immune effector cell-mediated B-cell cytotoxicity," Blood. vol. 115(22):4393-4402 (2010).

(Continued)

*Primary Examiner* — Jessica H Roark
*Assistant Examiner* — Francesca Edgingtongiordano
(74) *Attorney, Agent, or Firm* — Clark & Elbing LLP; Karen L. Elbing (57) ABSTRACT

The present disclosure relates to administration speed of obinutuzumab.

24 Claims, 7 Drawing Sheets
Specification includes a Sequence Listing.

(56) References Cited

OTHER PUBLICATIONS

Sehn et al. "Obinutuzumab plus bendamustine versus bendamustine monotherapy in patients with rituximab-refractory indolent non-Hodgkin lymphoma (GADOLIN): a randomised, controlled, open-label, multicentre, phase 3 trial ," Lancet Oncol. vol. 17 (8): 1081-1093 (2016).
Tobinai et al. "A Review of Obinutuzumab (GA101), a Novel Type II Anti-CD20 Monoclonal Antibody, for the Treatment of Patients with B-Cell Malignancies," Adv Ther. vol. 34(2):324-356 (2017).
Tsujimura et al. "Safety and Tolerability of Obinutuzumab (GA101) with Slhrter Duration of Infusion in Japanese Patients with Previously Untreated CD20-Positive & Cell Non-Hodgkin's Lymphoma (NHL)-Comparison with GA04915g (Gather) and B021005 (Goya) Studies," Blood. vol. 128: 1-6 (2016).

* cited by examiner

Obinutuzumab (GA101; G)

- Obinutuzumab (GA101; G)
  - Glycoengineered type II anti-CD20 mAb
  - Greater direct cell death induction and ADCC/ADCP activity than R[1,2]

ADCC, antibody-dependent cell-mediated cytotoxicity; ADCP, antibody-dependent cellular phagocytosis 1. S. Herter, et al. Mol Cancer Ther 2013
2. E. Mössner, et al. Blood 2010

Length of administration time and risk of IRR

Considering a heavy strain on patients, shorter duration of infusion (SDI) (subsequent infusions 3.25 hrs ⇒ 1.5 hrs) may increase the clinical usefulness of obinutuzumab.

<Length of administration time>

In phase 1 study (JO21900 study), which evaluated the safety, tolerability, PK and preliminary efficacy of obinutuzumab in Japanese patients, all 12 patients who were administered obinutuzumab experienced infusion-related reaction (IRR) at Cycle 1 Day 1.

K. Hatake JSH 2010

Summary of GATS study

| Objective | To confirm acceptability of obinutuzumab shorter duration of infusion (SDI) in Japanese patients |
|---|---|
| Target population | Previously untreated patients with CD20-positive B-cell NHL (DLBCL, FL, MZL) |
| Study design* | • Phase II, Multicenter, Open-label, Single-arm, G-CHOP × 8 Cycle |
| Primary endpoint | • Incidence rate of ≥Grade 3 infusion-related reactions in Cycle 2<br>• Serum concentrations and pharmacokinetic parameters of obinutuzumab<br>• Time course of cytokines (TNFα, IFNγ, IL-6, IL-8, IL-10) |
| Target # of patients | 36 patients |

GATS study design

*if patients meet the SDI inclusion criteria
SDI inclusion criteria
1. At least 3 consecutive doses of obinutuzumab by regular infusion without any ≥Grade 3 infusion-related reactions.
2. Pre-SDI peripheral lymphocyte count <5000/μL.

※CHOP therapy was designed to be administered on Day 1 of Cycle 1 to Cycle 6.

Study drug administration and SDI inclusion criteria were designed on the basis of GATHER study[1], which evaluated the safety and efficacy of G-CHOP.

1) A. Zelenetz Blood 2013

Patient characteristics (n=35)

| Age | Median | 66.0 | |
|---|---|---|---|
| | Range | 35 - 78 | |
| Sex | Male | 23 | (66%) |
| | Female | 12 | (34%) |
| PS | 0 | 28 | (80%) |
| | 1 | 6 | (17%) |
| | 2 | 1 | ( 3%) |
| Histology | DLBCL | 19 | (54%) |
| | FL | 13 | (37%) |
| | MZL | 1 | ( 3%) |
| | Other | 2 | ( 6%) |
| Ann Arbor Stage | I | 4 | (11%) |
| | II | 9 | (26%) |
| | III | 7 | (20%) |
| | IV | 15 | (43%) |

Safety profile (n=35)

| | # of patients | (Rate) |
|---|---|---|
| Total number of patients with at least one adverse event | 35 | (100%) |
| Grade 3-5 | 30 | ( 86%) |
| - related to obinutuzumab | 29 | ( 83%) |
| Serious AE | 9 | ( 26%) |
| - related to obinutuzumab | 9 | ( 26%) |
| Infusion-related reactions | 17 | ( 49%) |
| - Cycle 1 Day 1 | 15 | ( 43%) |
| - Cycle 1 Day 8 | 1 | ( 3%) |
| - Cycle 1 Day 15 | 2 | ( 6%) |
| - after Cycle 2 (incl. SDI) | 2 | ( 6%) |
| Infusion-related reactions (Grade 3-5) | 0 | |

No ≥Grade 3 infusion-related reactions occurred in the SDI transition patients.

The safety profile under SDI was comparable to that under regular infusion.

Efficacy (evaluated without PET)

At the end of treatment*

| | DLBCL (n=19)<br>(# of patients) | FL (n=13)<br>(# of patients) |
|---|---|---|
| ORR | 13 (68%) | 10 (77%) |
| CR | 11 (58%) | 8 (62%) |
| PR | 2 (11%) | 2 (15%) |
| SD | 0 ( 0%) | 1 ( 8%) |
| PD | 4 (21%) | 2 (15%) |
| NE | 2 (11%) | 0 ( 0%) |

*Assessed using the Revised Response Criteria for Malignant Lymphoma
(Cheson BD, et al. J Clin Oncol 2007)

Conclusion

- No ≥Grade 3 IRR occurred in the SDI transition patients.
  - IRR occurred most commonly on C1D1 under regular infusion, but all were Grade 1 or 2.
  - 3 IRR were observed under SDI in Cycle 6, 7, and 8, but all were classified as Grade 1.
  - Similar tendency was observed in GATHER study.

- Administration time and ethnic differences do not seem to have any effect on the PK of obinutuzumab.

- Cytokine elevation was observed during the first obinutuzumab infusion, but immediately decreased at the end of the infusion.

SDI of obinutuzumab over 90 mins was shown to be acceptable.

TREATMENT OF CD20-POSITIVE B-CELL LYMPHOMA WITH OBINUTUZUMAB

TECHNICAL FIELD

The present invention relates to administration speed of obinutuzumab.

BACKGROUND ART

Figure 1:
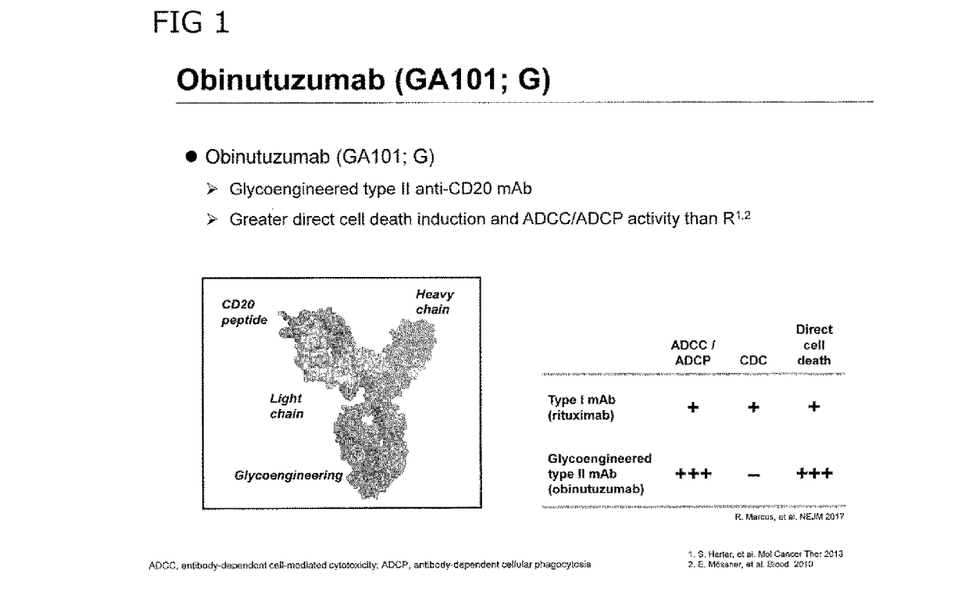
FIG. 1 shows characters of obinutuzumab. Obinutuzumab is a glycoengineered type II anti-CD20 mAb and has greater direct cell death induction and ADCC/ADCP activity than rituximab. ADCC, antibody-dependent cell-mediated cytotoxicity; ADCP, antibody-dependent cellular phagocytosis.

Obinutuzumab is a glycoengineered, type II anti-CD20 monoclonal antibody indicated for the treatment of B-cell malignancies. It differs from its predecessor rituximab by having lower complementdependent cytotoxicity but enhanced antibody-dependent cytotoxicity and direct B-cell death (NPL1-3, FIG. 1). In the phase III GALLIUM trial, which compared chemotherapy combined with either obinutuzumab or rituximab followed by anti-CD20 antibody maintenance therapy, obinutuzumab-based immunochemotherapy resulted in a clinically meaningful improvement in pro-gression-free survival in patients with previously untreated follicular lymphoma (FL) (NPL4, 5). Obinutuzumab plus bendamustine followed by obinutuzumab maintenance also improved efficacy over bendamustine monotherapy in rituximab-refractory patients with indolent B-cell non-Hodgkin lymphoma (NHL) in the phase III GADOLIN study (NPL 6).

CITATION LIST

Non Patent Literature

[NPL1] Mossner E, Brunker P, Moser S, et al. Increasing the efficacy of CD20 antibody therapy through the engineering of a new type II anti-CD20 antibody with enhanced direct and immune effector cell-mediated B-cell cytotoxicity. Blood 2010; 115:4393-402.

[NPL2] Herter S, Herting F, Mundigl O, et al. Preclinical activity of the type II CD20 antibody GA101 (obinutuzumab) compared with rituximab and ofatumumab in vitro and in xenograft models. Mol Cancer Ther 2013; 12:2031-42.

[NPL3] Tobinai K, Klein C, Oya N, Fingerle-Rowson G. A review of obinutuzumab (GA101), a novel type II anti-CD20 monoclonal antibody, for the treatment of patients with B-cell malignancies. Adv Ther 2017; 34:324-56.

[NPL4] Marcus R, Davies A, Ando K, et al. Obinutuzumab for the first-line treatment of follicular lymphoma. N Engl J Med 2017; 377:1331-44.

[NPL5] Hiddemann W, Barbui A M, Canales Albendea M A, et al. Immunochemotherapy with obinutuzumab or rituximab in previously untreated folllicular lymphoma in the randomised phase III GALLIUM study: analysis by chemotherapy regimen. Hematol Oncol 2017; 35:117-9.

[NPL6] Sehn L H, Chua N, Mayer J, et al. Obinutuzumab plus bendamustine versus bendamustine monotherapy in patients with rituximab-refractory indolent non-Hodgkin lymphoma (GADOLIN): a randomised, controlled, open-label, multicentre, phase 3 trial. Lancet Oncol 2016; 17:1081-93.

SUMMARY OF INVENTION

Figure 2:
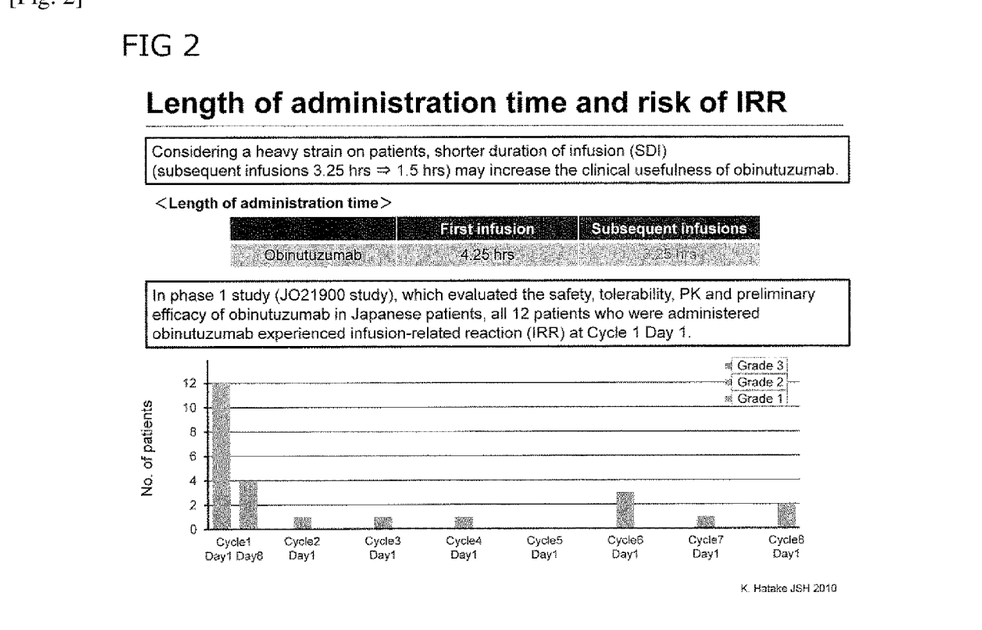
FIG. 2 shows length of administration time and risk of IRR. Considering a heavy strain on patients, realization of SDI will increase the clinical usefulness of obinutuzumab. In phase 1 study (JO21900 study), which evaluated the safety, tolerability, PK and preliminary efficacy of obinutuzumab in Japanese patients, all 12 patients who were administered obinutuzumab experienced infusion-related reaction (IRR) at Cycle 1 Day 1.

Obinutuzumab is currently given by intravenous (abbreviated as 'IV' in this description) infusion. Lengthy and/or frequent IV infusions are burdensome and inconvenient for patients and result in the need for lengthy observation times with increased nursing and administration staff workloads. Regular IV infusion (abbreviated as 'RI' in this description) of obinutuzumab takes approximately 3 to 4 h, and it is reasonable to consider that reducing the duration of infusion has potential advantages in terms of patient convenience, and more efficient use of healthcare facilities and staff time (FIG. 2). The main potential disadvantage of a shorter duration of infusion (abbreviated as 'SDI' in this description) lies in the possibility of increased risk of infusion related reactions (IRRs) mediated by cytokine release. However, studies in patients with rheumatoid arthritis or B-cell NHL have shown reduction of rituximab infusion times from at least 4 h to 1.5-2 h to be feasible, which has in turn led to the recommendation to increase infusion rates for rituximab and, similarly, to the investigation of SDI in patients receiving obinutuzumab.

SDI was also investigated in the GATHER trial, a phase II, open-label, multicenter, single-arm study of obinutuzumab in combination with cyclophosphamide, doxorubicin, vincristine and prednisolone (abbreviated as 'CHOP' in this description, where prednisolone is exchangeable for prednisone) chemotherapy in 80 previously untreated patients with CD20-positive advanced diffuse large B-cell lymphoma (abbreviated as 'DLBCL' in this description). Both of the SDI times evaluated in GATHER, 120 and 90 min, were well tolerated, with no IRRs of grade $\geq 3$. Overall, 4% of the GATHER population was of Asian ethnicity, and ethnic differences in the frequency of polymorphisms in genes involved in drug metabolic pathways have been suggested to be associated with changes in enzyme activity that might affect drug pharmacokinetics (abbreviated as 'PK' in this description). However, data obtained in various geographic populations receiving obinutuzumab have shown no relevant differences in the PK of obinutuzumab in Asian (including Chinese and Japanese) and non-Asian patients.

Figure 3:
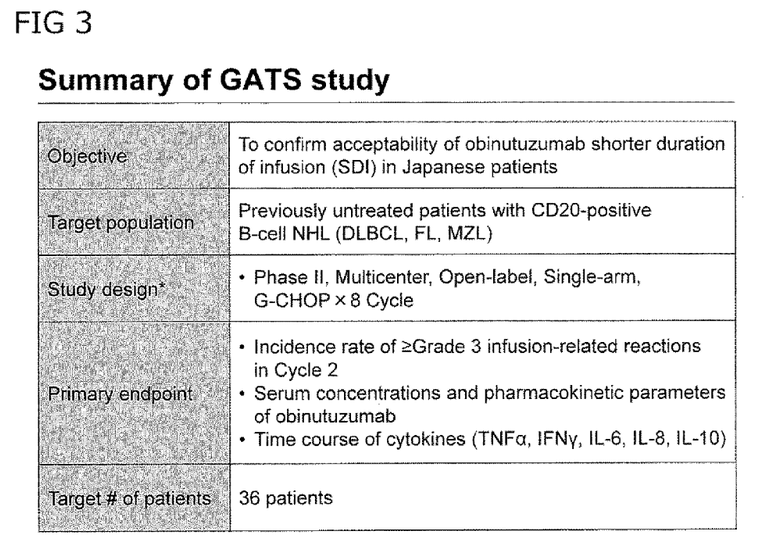
FIG. 3 shows summary of GATS study. Objective, to confirm acceptability of obinutuzumab shorter duration of infusion (SDI) in Japanese patients. Target population, previously untreated patients with CD20-positive B-cell NHL (DLBCL, FL, MZL). Study design, Phase II, Multicenter, Open-label, Single-arm, G-CHOP×8 Cycle. Primary endpoint, Incidence rate of Grade 3 infusion-related reactions in Cycle 2; Serum concentrations and pharmacokinetic parameters of obinutuzumab; time course of cytokines (TNFα, IFNγ, IL-6, IL-8, IL-10). Target number of patients, 36 (enrolled).

To explore these concepts further, the phase II GATS study (J029737, JapicCTI-152 848) was carried out to investigate the tolerability of obinutuzumab given using SDI in previously untreated patients with CD20-positive B-cell NHL, in particular the rate of grade IRRs, and to evaluate serum obinutuzumab concentrations and PK, and the time course of cytokine release (FIG. 3).

Specifically, the present invention relates to:

[1] A pharmaceutical composition for treating CD20-positive B-cell lymphoma comprising obinutuzumab, which is intravenously drip infused at 1000 mg of obinutuzumab per administration, and given according to the administration speeds of the following (a) and (b) in two or more cycles:
  (a) the maximum administration speed in the first cycle is equal to or more than 200 mg of obinutuzumab an hour, preferably equal to or more than 300 mg of obinutuzumab an hour, more preferably equal to or more than 400 mg of obinutuzumab an hour;
  (b) the maximum administration speed in the second or later cycle is equal to or more than 700 mg of obinutuzumab an hour, preferably equal to or more than 800 mg of obinutuzumab an hour, more preferably equal to or more than 900 mg of obinutuzumab an hour.

[2] The pharmaceutical composition according to [1], wherein a duration per administration in the second or later cycle is within 180 minutes, preferably within 150 minutes, more preferably within 120 minutes, the most preferably within 90 minutes.

[3] The pharmaceutical composition according to [1] or [2], which is administered 3 times in the first cycle, and once a cycle in the second or later cycle.

[4] The pharmaceutical composition according to [3], wherein the first administration in the first cycle is initiated at a speed of 50 mg of obinutuzumab an hour, and the second or later administration in the first cycle is initiated at a speed of 100 mg of obinutuzumab an hour.

[5] The pharmaceutical composition according to any one of [1] to [4], wherein the administration speed in the second or later cycle is increased to 700 mg of obinutuzumab an hour or faster, preferably to 800 mg of obinutuzumab an hour or faster, more preferably up to 900 mg of obinutuzumab an hour.

[6] The pharmaceutical composition according to any one of claims 1 to 5, wherein, in (b), the pharmaceutical composition is given according to at least one of the following (c) to (e) conditions:
  (c) if no infusion reaction of Grade 3 or above appeared with the last three administrations, and the number of lymphocytes in peripheral blood before administration is less than 5000/μL, administration is carried out at 100 mg/hour for 30 minutes. If no infusion reaction is observed all that time, the speed can be increased to 900 mg/hour. Depending on the condition of the patient, the speed is decreased to, for example, the administration speed in cycle 1, as appropriate.
  (d) if an infusion reaction of Grade 1/2 appeared, administration is restarted at half the speed before administration was stopped. If no infusion reaction is observed in 30 minutes, the speed can be increased to 900 mg/hour.
  (e) if an infusion reaction of Grade 3, administration is restarted at 200 mg/hour or lower. If no infusion reaction is observed in 30 minutes, the speed can be increased by 50 mg/hour every 30 minutes to a maximum of 400 mg/hour.

[7] The pharmaceutical composition according to any one of [1] to [6], which is administered on days 1, 8 and 15 in the first cycle, and on day 1 in the second or later cycle.

[8] The pharmaceutical composition according to any one of [1] to [7], wherein each cycle is 3 weeks.

[9] The pharmaceutical composition according to any one of [1] to [7], which is used in combination with at least one of other anti-tumor agents, and whose administration cycle is synchronized with a dosing cycle of said at least one of other anti-tumor agents, wherein the dosing cycle is 4 weeks a cycle.

[10] The pharmaceutical composition according to [9], wherein said at least one of other anti-tumor agents is selected from CHOP, CVP, bendamustine, fludarabine, lenalidomide, an anti-PD-1 antibody, and an anti-PD-L1 antibody.

[11] The pharmaceutical composition according to any one of [1] to [10], wherein the pharmaceutical composition is given every two months for two years as maintenance monotherapy after said two or more cycles.

[12] The pharmaceutical composition according to any one of [1] to [11], wherein the obinutuzumab concentration in infusion fluid when intravenously drip infused is 10 to 40 mg/mL, preferably 20 to 30 mg/mL, more preferably 25 mg/mL.

[13] The pharmaceutical composition according to any one of [1] to [12], further comprising a trehalose hydrate, L-histidine, L-histidine hydrochloride hydrate, or polyoxyethylene (160) polyoxypropylene (30) glycol as an additive.

[14] Use of obinutuzumab in a manufacture of a pharmaceutical composition for treating CD20-positive B-cell lymphoma comprising obinutuzumab, wherein the composition is intravenously drip infused at 1000 mg of obinutuzumab per administration, and given according to the administration speeds of the following (a) and (b) in two or more cycles:
  (a) the maximum administration speed in the first cycle is equal to or more than 200 mg of obinutuzumab an hour, preferably equal to or more than 300 mg of obinutuzumab an hour, more preferably equal to or more than 400 mg of obinutuzumab an hour;
  (b) the maximum administration speed in the second or later cycle is equal to or more than 700 mg of obinutuzumab an hour, preferably equal to or more than 800 mg of obinutuzumab an hour, more preferably equal to or more than 900 mg of obinutuzumab an hour.

[15] A method for treating CD20-positive B-cell lymphoma by a pharmaceutical composition comprising obinutuzumab, wherein the composition is intravenously drip infused at 1000 mg of obinutuzumab per administration, and given according to the administration speeds of the following (a) and (b) in two or more cycles:
  (a) the maximum administration speed in the first cycle is equal to or more than 200 mg of obinutuzumab an hour, preferably equal to or more than 300 mg of obinutuzumab an hour, more preferably equal to or more than 400 mg of obinutuzumab an hour;
  (b) the maximum administration speed in the second or later cycle is equal to or more than 700 mg of obinutuzumab an hour, preferably equal to or more than 800 mg of obinutuzumab an hour, more preferably equal to or more than 900 mg of obinutuzumab an hour.

DETAILED DESCRIPTION OF THE INVENTION

Description of Embodiments

I. Summary regarding dosage and administration of obinutuzumab.

In the present application, obinutuzumab is a glycoengineered, genetically recombined and humanized anti-CD20 monoclonal antibody, a glycoprotein that exhibits the characteristics of a type II anti-CD20 antibody and comprises two heavy chains of 449 amino acid residues and two light chains of 219 amino acid residues, and has a molecular weight of about 148,000-150,000. Specifically, obinutuzumab in the present application includes not only those specified under "Obinutuzumab (Genetical Recombination)" in Japanese Accepted Names for Pharmaceuticals (JAN) but also biosimilar and biobetter products thereof.

Below, a pharmaceutical composition comprising obinutuzumab shall be referred to as "present formulation".

<Effects and Efficacy>

Examples of the "effects and efficacy" of the present formulation are provided below as one embodiment.

An example of a disease targeted by the present formulation is CD20-positive B-cell lymphoma. That is, the present formulation is a pharmaceutical composition for treating CD20-positive B-cell lymphoma comprising obinutuzumab. Examples of CD20-positive B-cell lymphoma include follicular lymphoma, low-grade lymphoma, intermediate-grade lymphoma, and high-grade lymphoma. The CD20-positive B-cell lymphoma is preferably CD20-positive B-cell follicular lymphoma.

<Dosage and Administration>

Examples of the "dosage and administration" of the present formulation are provided below as one embodiment. The dosage and administration tolerability, including administration speed, illustrated below, has been demonstrated by the GATS study.

Normally, obinutuzumab is intravenously drip infused at 1000 mg per administration in adults.

For induction therapy, each cycle is three weeks, and administration is performed on days 1, 8 and 15 in cycle 1, and on day 1 in cycles 2 to 8. Where an anti-tumor agent is used in combination and is administered in four-week intervals, each cycle is four weeks, and administration is performed on days 1, 8 and 15 in cycle 1, and on day 1 in cycles 2 to 6.

After 24 weeks of induction therapy, maintenance therapy is carried out by administering the present formulation alone every two months for two years.

The present formulation is administered at the following administration speed. Moreover, grading criteria are in accordance with NCI-CTCAE ver. 4.03.

(On First Administration)

Intravenous drip infusion is initiated at a speed of 50 mg/hour. The speed is increased by 50 mg/hour every 30 minutes while the patient's condition is adequately monitored, and can be raised to a maximum of 400 mg/hour.

(On or after Second Administration in Cycle 1)

If no infusion reaction of Grade 2 or above appeared with the previous administration, administration is initiated at 100 mg/hour, and if no infusion reaction is observed, the speed can be increased by 100 mg/hour every 30 minutes to a maximum of 400 mg/hour.

(In or after Cycle 2)

If no infusion reaction of Grade 3 or above appeared with the last three administrations, and the number of lymphocytes in peripheral blood before administration is less than 5000/ μL, administration is carried out at 100 mg/hour for 30 minutes. If no infusion reaction is observed, the speed can be increased to 900 mg/hour. Depending on the condition of the patient, the speed is decreased to, for example, the administration speed in cycle 1, as appropriate.

If an infusion reaction appeared, the following response is taken.

(If an Infusion Reaction of Grade 2 or Below Appeared)

Administration is stopped or the administration speed is decreased.

(If an Infusion Reaction of Grade 3 Appeared)

Administration is stopped and appropriate measures are taken.

If administration was stopped, after the patient has recovered/remitted from the infusion reaction, the administration speed is adjusted and administration is restarted as described below.

(If an Infusion Reaction of Grade 4 Appeared)

Administration of the present formulation is stopped immediately, and appropriate measures are taken.

(If an Infusion Reaction of Grade 3 Recurred and if an Infusion Reaction of Grade 4 Appeared)

The present formulation will not be administered again. When administration is restarted after administration was stopped following an infusion reaction, the administration speed at the time of restart is handled as follows.

(On First Administration and on or after Second Administration in Cycle 1)

Administration is restarted at half the speed before administration was stopped. If no infusion reaction is observed in 30 minutes, the speed can be increased by 50 mg/hour every 30 minutes to a maximum of 400 mg/hour.

(If an Infusion Reaction of Grade 1/2 Appeared in or after Cycle 2)

Administration is restarted at half the speed before administration was stopped. If no infusion reaction is observed in 30 minutes, the speed can be increased to 900 mg/hour.

(If an Infusion Reaction of Grade 3 Appeared in or after Cycle 2)

Administration is restarted at 200 mg/hour or lower. If no infusion reaction is observed in 30 minutes, the speed can be increased by 50 mg/hour every 30 minutes to a maximum of 400 mg/hour.

II. Pharmaceutical Composition

A pharmaceutical composition in the present invention comprises obinutuzumab. In one embodiment, the pharmaceutical composition comprises a pharmaceutically effective amount of obinutuzumab. Obinutuzumab is a glycoengineered, genetically recombined and humanized anti-CD20 monoclonal antibody, a glycoprotein that exhibits the characteristics of a type II anti-CD20 antibody and comprises two heavy chains of 449 amino acid residues and two light chains of 219 amino acid residues, and has a molecular weight of about 148,000-150,000. Specifically, obinutuzumab in the present application includes not only those specified under "Obinutuzumab (Genetical Recombination)" in Japanese Accepted Names for Pharmaceuticals (JAN), but also biosimilar in which the amino acid sequence of a heavy chain is revealed in SEQ No. 1 and the amino acid sequence of a light chain is revealed in SEQ No. 2, and biobetter products thereof originating from those amino acids sequences.

The pharmaceutical composition is used for treating CD20-positive B-cell lymphoma comprising. Examples of the CD20-positive B-cell lymphoma include follicular lymphoma, low-grade lymphoma, intermediate-grade lymphoma, and high-grade lymphoma. The CD20-positive B-cell lymphoma is preferably CD20-positive B-cell follicular lymphoma.

In one embodiment, the concentration of obinutuzumab in the pharmaceutical composition as infusion fluid when intravenously drip infused is normally 10 to 40 mg/mL. In another embodiment, the concentration is 20 to 30 mg/mL. In another embodiment, the concentration is 25 mg/mL. In a preferred embodiment, the concentration is 20 to 30 mg/mL. In a more preferred embodiment, the concentration is 25 mg/mL.

In one embodiment, the pharmaceutical composition may further comprise at least one additive selected from a trehalose hydrate, L-histidine, L-histidine hydrochloride hydrate, or polyoxyethylene (160) polyoxypropylene (30) glycol. In a preferred embodiment, the pharmaceutical composition comprise a trehalose hydrate, L-histidine, L-histidine hydrochloride hydrate, and polyoxyethylene (160) polyoxypropylene (30) glycol as additives.

In one embodiment, the pharmaceutical composition is administered in two or more cycles. A period of the cycle may be decided in 3 to 5 weeks by one of ordinary skill in the art. Example of the period is 3 weeks or 4 weeks. In the case that the pharmaceutical composition is administered as monotherapy, the period is preferably 3 weeks. In the case that the pharmaceutical composition is administered in combination with at least one of anti-tumor agents, the period is preferably 4 weeks. When the pharmaceutical composition is combined with such anti-tumor agent(s), administration cycles of the pharmaceutical composition are preferably synchronized with dosing cycles of the anti-tumor agent(s).

In one embodiment, administration frequency of the pharmaceutical composition is normally once or more times per cycle. The frequency is altered each cycle. In another embodiment, the pharmaceutical composition is administered 3 times in the first cycle. In another embodiment, the pharmaceutical composition is administered once a cycle in the second or later cycle. In preferred embodiment, the pharmaceutical composition is administered 3 times in the first cycle, and once a cycle in the second or later cycle.

In one embodiment, administration date in a cycle is arranged by one of ordinary skill in the art. In another embodiment, the date is on days 1, 8 and 15 in the first cycle, and on day 1 in the second or later cycle.

In one embodiment, an amount of obinutuzumab per administration is altered by one of ordinary skill in the art within the range of 1 to 2000 mg. In a specific embodiment, the pharmaceutical composition is intravenously drip infused at 1000 mg of obinutuzumab per administration.

In one embodiment, the pharmaceutical composition is given according to the administration speeds of the following (a) and (b) in two or more cycles.

(a) the maximum administration speed in the first cycle is equal to or more than 200 mg of obinutuzumab an hour, preferably equal to or more than 300 mg of obinutuzumab an hour, or more preferably equal to or more than 400 mg of obinutuzumab an hour.

(b) the maximum administration speed in the second or later cycle is equal to or more than 700 mg of obinutuzumab an hour, preferably equal to or more than 800 mg of obinutuzumab an hour, or more preferably equal to or more than 900 mg of obinutuzumab an hour.

In another embodiment of the above (a), the maximum administration speed in the first cycle is preferably equal to or more than 300 mg of obinutuzumab an hour, or more preferably equal to or more than 400 mg of obinutuzumab an hour.

In another embodiment of the above (b), the maximum administration speed in the second or later cycle is preferably equal to or more than 800 mg of obinutuzumab an hour, or more preferably equal to or more than 900 mg of obinutuzumab an hour. In the embodiment, a duration per administration in the second or later cycle is preferably within 180 minutes. The duration is preferably within 150 minutes, more preferably within 120 minutes, or the most preferably within 90 minutes.

In one embodiment, the first administration in the first cycle is initiated at a speed of 50 mg of obinutuzumab an hour. The second or later administration in the first cycle is initiated at a speed of 100 mg of obinutuzumab an hour.

In one embodiment, the administration speed in the second or later cycle is increased to 700 mg of obinutuzumab an hour or faster, preferably to 800 mg of obinutuzumab an hour or faster, more preferably up to 900 mg of obinutuzumab an hour.

In other embodiment, when the pharmaceutical composition is combined with antitumor agent(s), at least one agent is appropriately chosen from heretofore known agents. The other anti-tumor agent is at least one selected from CHOP, CVP, bendamustine, fludarabine, lenalidomide, an anti-PD-1 antibody, and an anti-PD-L1 antibody.

In one embodiment, maintenance monotherapy by obinutuzumab is performed as an additional therapy. The maintenance monotherapy is performed every two months for two years after treatment by the pharmaceutical composition, the treatment is referred to as 'induction therapy' in this case.

III. Production Method

Obinutuzumab can be manufactured by aritisan of ordinary skill according to known methods as shown in WO2005/044859. The pharmaceutical composition is also manufactured by mixing obinutuzumab with other ingredients by ordinal skill.

This invention also provides use of obinutuzumab in a manufacture of a pharmaceutical composition for treating CD20-positive B-cell lymphoma. The pharmaceutical composition is administered in the same manner as mentioned in 'II. Pharmaceutical composition'.

IV. Treatment Method

This invention also provides a method for treating CD20-positive B-cell lymphoma by a pharmaceutical composition comprising obinutuzumab. In the method, the pharmaceutical composition intravenously drip infused at 1000 mg of obinutuzumab per administration, and given according to the administration speeds of the following (a) and (b) in two or more cycles:

(a) the maximum administration speed in the first cycle is equal to or more than 200 mg of obinutuzumab an hour, preferably equal to or more than 300 mg of obinutuzumab an hour, more preferably equal to or more than 400 mg of obinutuzumab an hour;

(b) the maximum administration speed in the second or later cycle is equal to or more than 700 mg of obinutuzumab an hour, preferably equal to or more than 800 mg of obinutuzumab an hour, more preferably equal to or more than 900 mg of obinutuzumab an hour.

A method to use the pharmaceutical composition is the same as mentioned in 'II. Pharmaceutical composition'.

It hasn't been cleared whether or not SDI is suitable for administration of obinutuzumab into human before the present invention, because possibility that glycoengineering in obinutuzumab causes any abnormal immunological reaction wasn't able to be denied. Overall, it has been found on the basis of GATS study that the aforementioned pharmaceutical composition is safely and tolerably administered, and can reduce treatment burden on patients and medical professions suffered from a long time administration in regular infusion.

EXAMPLES

<Overview of GATS Clinical Study>

Title: Safety and tolerability of obinutuzumab (GA101) SDI in Japanese non hodgkin's lymphoma patient Background: Obinutuzumab (GA101, G) is a novel anti-CD20 monoclonal antibody.

G-based immunochemotherapy resulted in a clinically meaningful improvement in progression-free survival (PFS) in patients (pts) with follicular lymphoma (FL) (ASH 2016, #6). Regular infusion (RI) of G takes approx. 3-4 hrs. Shortening the duration of administration may be more convenient for pts.

Methods: The GATS study (JapicCTI-152848) included pts with previously untreated CD20-positive B-cell non-Hodgkin's lymphoma. Treatment consisted of 8 cycles (C) of G, plus CHOP on C1-C6 (with additional G on Days 8 and 15 of C1). SDI was conducted from C2, with infusion of G over 90 min. The primary endpoints were tolerability of SDI, pharmacokinetics (PK), and cytokine release. Tolerability was assessed by incidence of infusion-related reactions (IRRs).

Results: Of 36 pts enrolled, 35 pts were treated, including 19 with diffuse large B-cell lymphoma, 13 with FL, and 3 with other histologies. Overall, 17/35 pts (49%) experienced IRRs. All were Grade 1/2 and occurred most commonly on C1 Day 1 (RI). 2 pts started SDI from C3 or C4 due to deviation or AE. Under SDI, 3 IRRs were observed, but all were Grade 1. Serum G level just after C2 under SDI was similar to that in C8. This shows that PK reached a steady state at C2 and was not affected by shortening of administration. Cytokine elevation was observed during the first G infusion, but immediately decreased at end of the infusion.

Conclusions: SDI of G over 90 min was acceptable in Japanese patients. PK and serum cytokine profiles were comparable to those under RI.

<Detail Description of GATS Clinical Study>

Study Design and Treatments

This was a phase II, multicenter, open-label, single-arm study conducted in Japan. Eligible patients were aged ≥20 years with previously untreated and histologically confirmed CD20-positive B-cell NHL (DLBCL, FL or marginal zone lymphoma); Eastern Cooperative Oncology Group performance status of 0-2; life expectancy ≥12 months from date of enrollment; adequate cardiovascular function defined as left ventricular ejection fraction ≥50%; adequate organ function defined as hemoglobin ≥9 g/dL, absolute neutrophil count ≥1.5×10$^9$ cells/l, peripheral lymphocytes <5.0×10$^9$ cells/l and platelet count ≥75×10$^9$ cells/l; serum bilirubin, serum creatinine and prothrombin time or activated partial thromboplastin time times ≤1.5 the site-specific upper limit and hepatic enzymes ≤2.5 times the site-specific upper limit. Patients were also required not to have undergone major surgery or to have received immune suppression therapy, live vaccine or other study drugs in the 4 weeks preceding enrollment; no monoclonal antibody treatment was permitted within the preceding 12 weeks.

Exclusion criteria included prior therapy for NHL (except for nodal biopsy or local irradiation); primary central nervous system (CNS) lymphoma, secondary CNS involvement or leptomeningeal lymphoma; recent (≤4 weeks) history of significant infection, other malignancy or history of autoimmune disease that could affect the results of the present study; ongoing corticosteroid treatment with the equivalent of prednisolone >30 mg/day for any condition other than lymphoma; any prior use of cytotoxic agents or rituximab or any other anti-CD20 antibody; positive tests for hepatitis B surface (HBs) antigen, HBs antibody, hepatitis B core (HBc) antibody, or hepatitis C virus (HCV) antibody; HIV or human T-cell lymphotropic virus type-I and uncontrolled diabetes mellitus. Patients with HBs antibodies clearly attributable to vaccination and who did not test positive for hepatitis B virus DNA regardless of antibody status were permitted to enroll, as were those who tested positive for HCV antibodies but who had HCV RNA-negative status. The study was approved by local Institutional Review Boards and was conducted in accordance with the Declaration of Helsinki and Good Clinical Practice. All patients gave written and informed consent.

Figure 4:
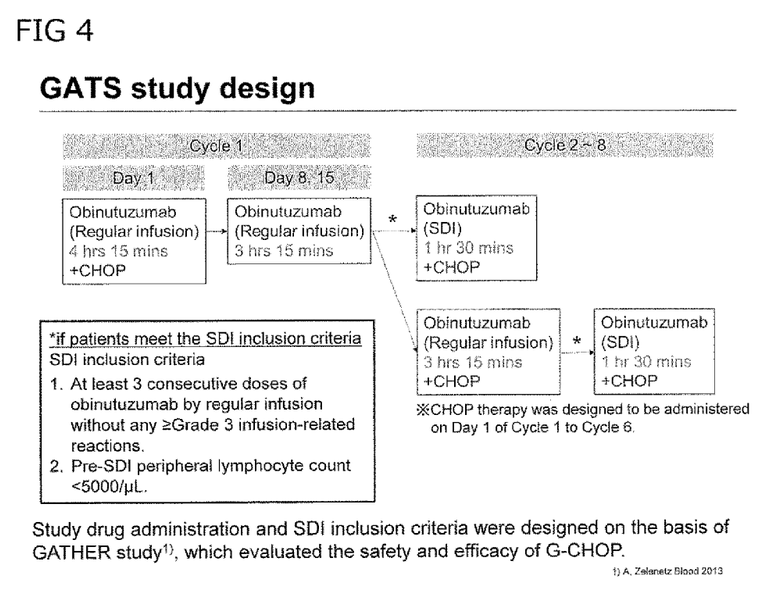
FIG. 4 shows clinical design of GATS study. Study drug administration and SDI inclusion criteria were designed on the basis of GATHER study, which evaluated the safety and efficacy of G-CHOP, and SDI was confirmed by GATS study. Obinutuzumab was administered by regular infusion with CHOP in day 1 of cycle 1, for 4 hours and 15 minutes, and in day 8 and 15 of the cycle 1, for 3 hours and 15 minutes. If patients meet the SDI inclusion criteria (at least 3 consecutive doses of obinutuzumab by regular infusion without any ≥Grade 3 infusion-related reactions; pre-SDI peripheral lymphocyte count <5000/ μL), obinutuzumab was administered by SDI in cycle 2 to 8.
Figure 5:
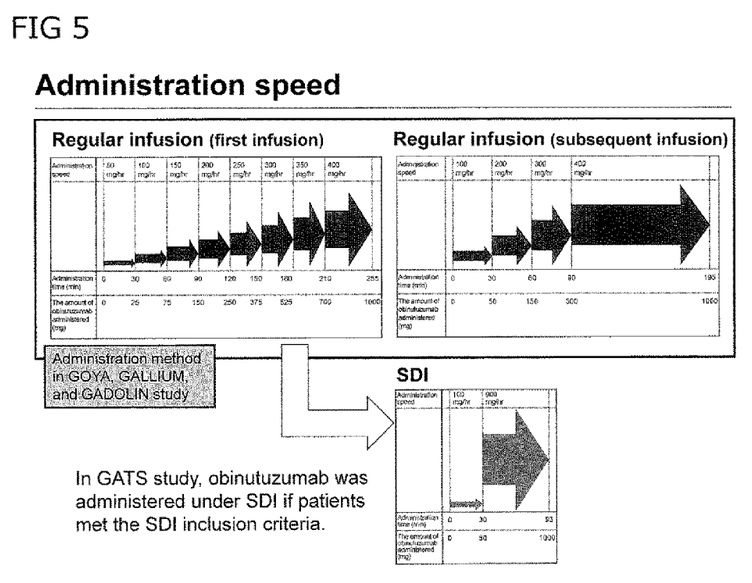
FIG. 5 shows comparison of administration speed between regular infusion and SDI in GATS study.

Treatment consisted of eight 21-day cycles of obinutuzumab, given as 1000 mg IV on Days 1, 8 and 15 of Cycle 1 plus standard CHOP on Day 1 of Cycles 1-6 (FIG. 4). Obinutuzumab was administered as RI in Cycle 1 (3-4 h), and then as a 90-min SDI from Cycle 2 in patients who met the SDI criteria (FIG. 5). The SDI criteria were to confirm patient safety at the RI rate and included no grade ≥3 IRR with a causal relationship to obinutuzumab treatment during any of the three RIs in Cycle 1 and a peripheral lymphocyte count <$5.0 \times 10^9$ cells/l before SDI was started. Patients who did not meet these criteria before Cycle 2 could still transition from RI to SDI if they met the criteria in any subsequent cycle.

Standard CHOP consisted of cyclophosphamide 750 mg/m$^2$, doxorubicin 50 mg/m$^2$ and vincristine 1.4 mg/m$^2$ IV on Day 1, and prednisolone 100 mg/day orally or IV on Days 1-5. When obinutuzumab and CHOP were scheduled to be administered on the same day, prednisolone was given prior to the obinutuzumab infusion. Dose reductions to suit the patient's condition were permitted.

Study Endpoints

The primary endpoints of the study were the incidence of grade ≥3 IRRs in Cycle 2 in patients who started SDI in Cycle 2, serum concentrations and PK parameters of obinutuzumab after SDI up to Day 12 of Cycle 2, and the time courses of cytokine release for tumor necrosis factor alpha (TNFα), interferon gamma (IFNγ) and interleukins 6, 8 and 10 (IL6, IL8 and IL10). IRRs were defined as adverse events (AEs) that were judged by the investigator to be related to obinutuzumab and that were reported during or within 24 h of an infusion.

Secondary endpoints included all other AEs (regardless of relationship to obinutuzumab treatment), IRRs reported during SDI, tumor response at the end of treatment and best response (at any time during follow-up).

The PK analysis population included all patients who received obinutuzumab by SDI on Cycle 2. PK parameters of obinutuzumab for each patient were estimated using non-compartmental analysis (NCA; Phoenix WinNonlin® version 6.4; Certara® USA, Inc.). The following PK parameters were calculated: maximum observed serum concentration (Cmax), area under the serum concentration-time curve from 0 to Day 7 ($AUC_{0-7}$), elimination half-life ($t_{1/2}$) and AUC from 0 to last measurable point ($AUC_{last}$).

Statistical and Analytical Methods

The sample size was based on estimates of the true probability that the incidence of grade ≥3 IRRs in Cycle 2 would exceed 5%. According to the estimates used, on the assumption that there was a grade ≥3 IRR in 1 patient, if 30 patients were recruited, the likelihood that the probability of an IRR would exceed 5% would be 2.2%. This figure was increased to 36 on the assumption that 20% of patients would not be able to make the transition to SDI. The sample size was therefore set at 36 patients.

The incidence rate of grade ≥3 IRRs in Cycle 2 was obtained by dividing the number of patients who developed such reactions by the number of SDI-transition patients. The probability of a grade ≥3 IRR occurring was determined according to the Bayesian approach, using the incidence of grade ≤3 IRRs in Cycle 2 of the GATHER study as the prior distribution. No differences were assumed to exist between Japanese and non-Japanese patients in the probability of developing a grade ≥3 IRR, regardless of infusion rate. We assumed that SDI was adequately tolerated if the true probability of developing a grade ≥3 IRR was ≤5%.

Summary statistics, including arithmetic mean, geometric mean, standard deviation, coefficient of variation, median, minimum and maximum, were calculated for cytokine concentrations at each study visit using serum cytokine concentrations from SDI-transition patients up to Cycle 2. Time courses of cytokine concentrations were also evaluated. The same summary data were generated for PK parameters based on serum obinutuzumab concentrations in SDI transition patients up to Day 12 of Cycle 2. NCA was used. Cycle 2 serum concentrations were compared with additional samples obtained before and after dosing at Cycle 8.

Patient Population

Figure 6:
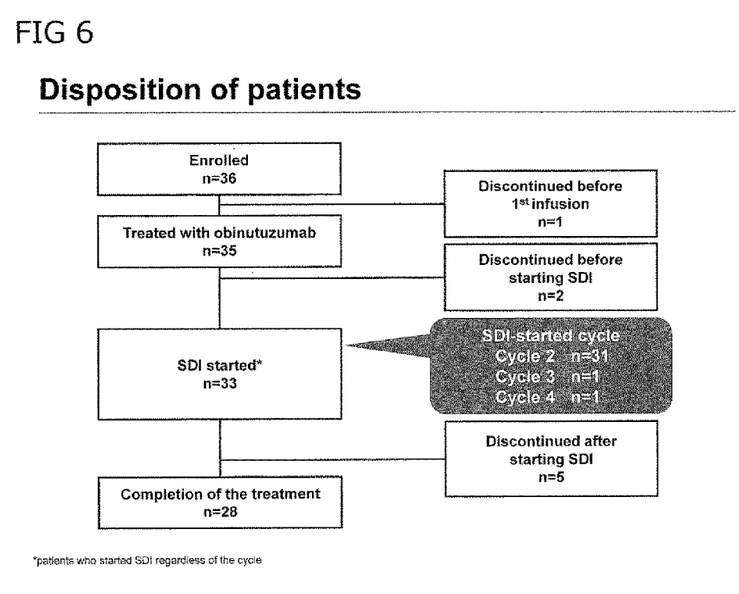
FIG. 6 shows disposition of patients in GATS study.

In total, 36 Japanese patients were enrolled, of whom 35 were treated (safety population; FIG. 6); 28 (80%) completed all eight cycles of treatment. Thirty-one patients started SDI in Cycle 2 (SDI-transition patients), and 2 further patients started SDI in subsequent cycles (1 in Cycle 3 and 1 in Cycle 4) to make a total of 33 SDI-treated patients. Two patients discontinued before starting SDI. Sufficient treatment intensity was achieved; median dose intensity of obinutuzumab was 100%.

Figure 7:
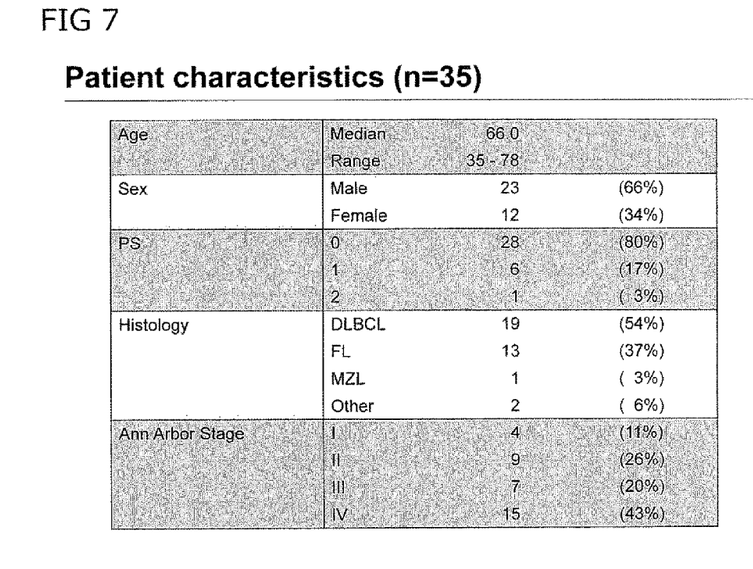
FIG. 7 shows patient characteristics in GATS study.

The median age of the patients was 66 years, with just over half of the study population aged between 60 and 70 years (FIG. 7). Approximately two-thirds were male, and the majority of patients had DLBCL (54%) or FL (37%). A fifth of patients (20%) had bone marrow involvement.

Infusion-Related Reactions

Overall, 17/35 patients (49% of the safety population) experienced a total of 21 IRRs; all were grade 1 or 2, and the majority [18/21 IRRs (86%)] occurred during Cycle 1 (in which RI was used). No SDI-associated IRRs occurred in SDI-transition patients in Cycle 2, so it was not possible to estimate the likelihood that the true probability of a grade ≥3 IRR in SDI-transition patients in Cycle 2 would exceed the 5% level inferred using the GATHER study data as the prior distribution. Furthermore, the likelihood that the true probability of a grade ≥3 IRR in SDI transition patients in Cycle 2 would exceed the 5% level inferred using the non-informative prior distribution was 0.05%. There were reports of two patients with IRRs during the SDI in Cycles 6, 7 and 8; all were of grade 1 severity (1 patient experienced nasopharyngitis in Cycle 6, and another experienced headache in Cycles 7 and 8 and palpitations in Cycle 7).

Other Safety and Tolerability Endpoints

Figure 8:
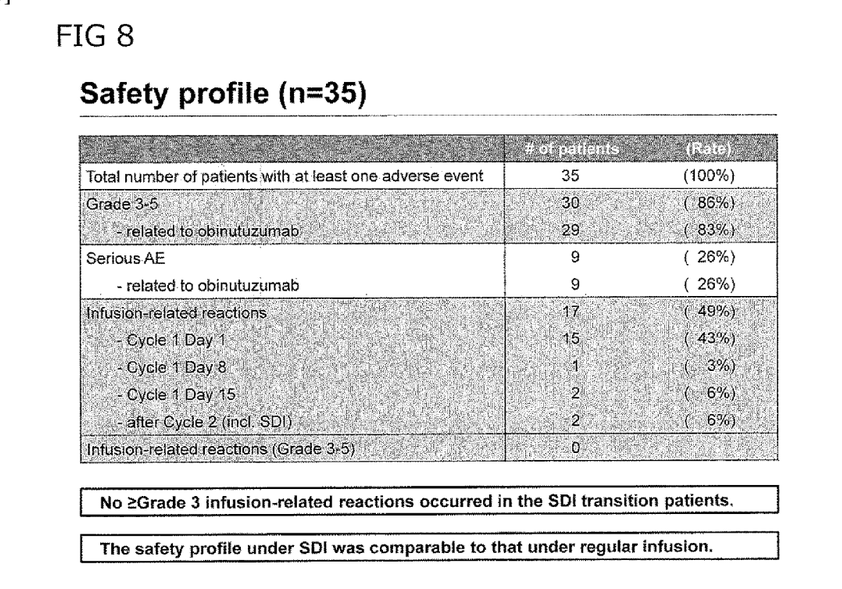
FIG. 8 shows safety profile in GATS study. No Grade 3 infusion-related reactions occurred in the SDI transition patients. The safety profile under SDI was comparable to that under regular infusion.

AEs were observed in all 35 patients (FIG. 8). All patients had at least one AE that was judged by the investigator to be treatment-related. Grade ≥3 AEs were observed in 30 patients (86%) and were judged treatment-related in 29 patients (83%). Blood and lymphatic system disorders (neutropenia, leukopenia and thrombocytopenia) were among the treatment-related grade ≥3 AEs most frequently reported. Serious AEs were reported in nine patients (26%). All were judged treatment-related.

Figure 10:
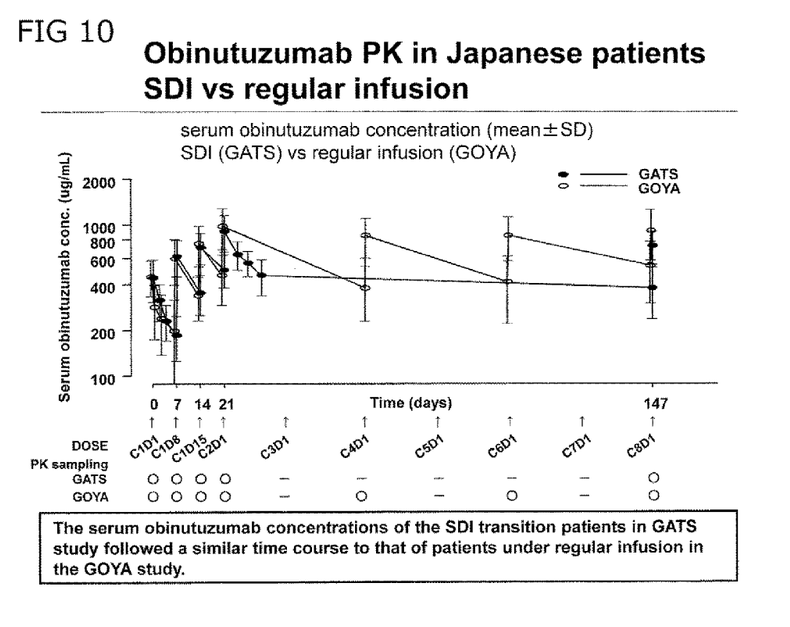
FIG. 10 shows obinutuzumab PK in Japanese patients after administration by SDI in GATS study versus regular infusion in GOYA study. The serum obinutuzumab concentrations of the SDI transition patients in GATS study followed a similar time course to that of patients under regular infusion in the GOYA study.

There were no AEs leading to death (grade 5) during the study. Obinutuzumab treatment was stopped in three patients because of AEs: one case each of infected dermal cyst, bronchiolitis and aspiration pneumonia. Aspiration pneumonia was not treatment-related. AEs leading to dose reduction or interruption of obinutuzumab treatment occurred in three patients, while AEs leading to dose reduction or interruption of any study drug occurred in nine patients. AEs leading to interruption of any study medication (n=4) were neutropenia, cellulitis, IRR, cerebral infarction or pneumonitis (1 each). Dose reduction of any study medication (n=7) was due to neutropenia/neutrophil count decreased (n=4), leukopenia/white blood cell count decreased (n=3), thrombocytopenia/platelet count decreased (n=3), alanine aminotransferase increased, aspartate aminotransferase increased, neuropathy peripheral, peripheral sensory neuropathy or steroid withdrawal syndrome (1 each).
Pharmacokinetics The serum obinutuzumab concentrations of the SDI transition patients in GATS study followed a similar time course to that of patients under regular infusion in the GOYA study (FIG. 10).

Figure 11:
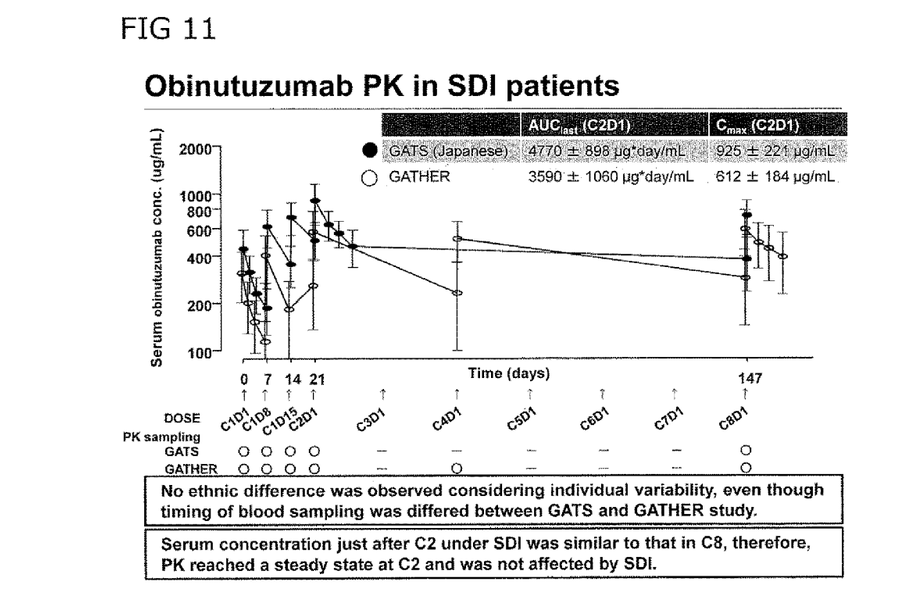
FIG. 11 shows obinutuzumab PK in SDI patients of GATS study and GATHER study. No ethnic difference was observed considering individual variability, even though timing of blood sampling was differed between GATS and GATHER studies. Serum concentration just after cycle 2 under SDI was similar to that in cycle 8, therefore, PK reached a steady state at cycle 2 and was not affected by SDI.
Figure 12:
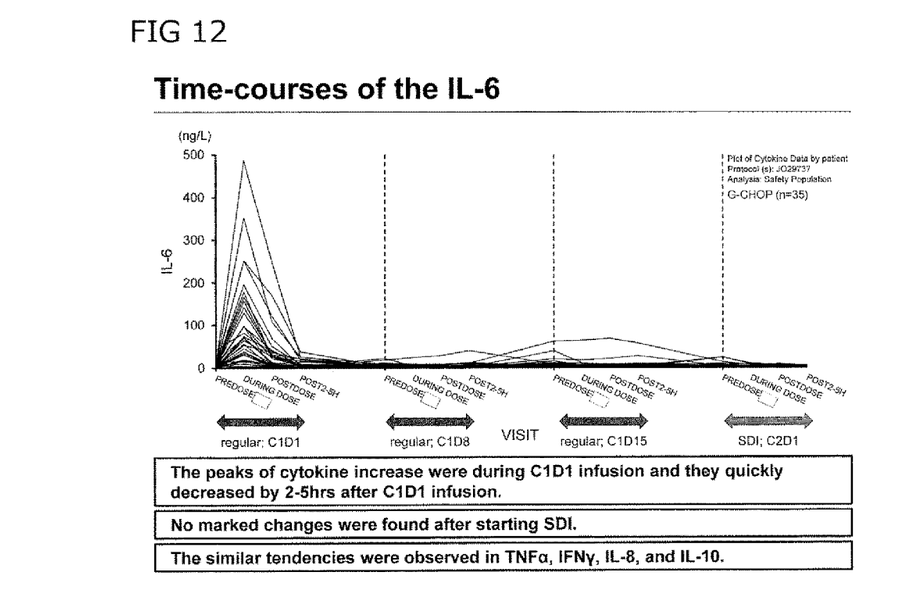
FIG. 12 shows IL-6 release after administration of obinutuzumab in GATS study. The peaks of cytokine increase were in infusion in day 1 of cycle 1 and they quickly decreased by 2-5 hours after the infusion. No marked changes were found after starting SDI. The similar tendencies were observed in TNFα, IFNγ, IL-8, and IL-10.
Figure 13:
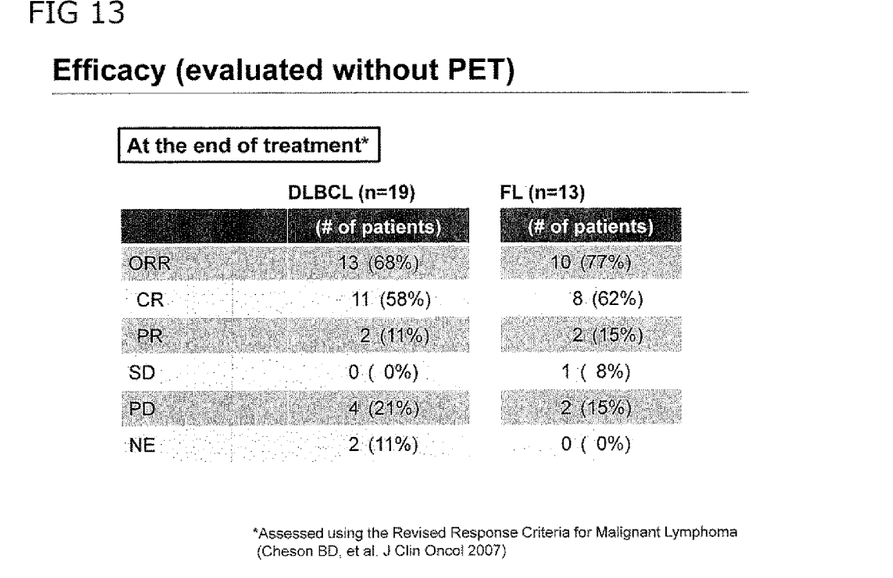
FIG. 13 shows treatment efficacy of obinutuzumab to DLBCL and FL in GATAS study.

The mean serum obinutuzumab concentration at Cycle 8 was similar to that in Cycle 2 in 17 evaluable SDI-transition patients. This indicates that steady-state PK were attained at Cycle 2 and were not affected by the reduced duration of infusion. The mean±standard deviation $AUC_{last}$ ($AUC_{7day}$) was 4 770±898 µg day/ml at Cycle 2 (vs. 3590±1060 µg day/ml at Cycle 8 in GATHER) (FIG. 11). The mean $t_{1/2}$ was 15.4±7.55 days (based on 17 evaluable SDI patients; vs. 23.0±15 days in GATHER). The $AUC_{last}$ ($AUC_{1day}$) value on Day 1 of Cycle 2 was 6790±1450 µg day/ml, with a Cmax of 925±221 µg/ml.
Cytokines For all 35 patients (including the 31 SDI-transition patients), cytokine elevations were observed during the first obinutuzumab infusion but were followed by an immediate decrease 2-5 h after the end of the infusion (FIG. 12 shows the case of IL6). No relevant changes were observed after starting SDI. There was also a rapid depletion in CD19-positive B-cells after the first obinutuzumab infusion. Counts decreased to <0.07×10$^9$ cells/l and remained at this level for the duration of the study. Efficacy The overall response rate on computed tomography-based assessment at the end of treatment was 77% (10/13) in patients with FL and 68% (13/19) in patients with DLBCL (including complete and partial responses; FIG. 13). The best overall responses were 92% (12/13) and 79% (15/19), respectively. Complete responses, CR, (without positron emission tomography scanning) were obtained in 8 of 13 patients with FL (62%) and 11 of 19 patients with DLBCL (58%) at the end of treatment, and in 8 of 13 patients with FL (62%) and 12 of 19 patients with DLBCL (63%) in the best complete response evaluation.

The current study aimed to investigate the tolerability (in particular the rate of IRRs), PK and cytokine release profile of SDI of obinutuzumab plus CHOP chemotherapy in patients with untreated CD20-positive B-cell NHL. The vast majority of IRRs with obinutuzumab plus CHOP were observed in Cycle 1 of treatment, during which RI was used. No IRRs of any grade were observed during Cycle 2, and only two patients experienced IRRs in subsequent cycles during treatment with obinutuzumab by SDI, which were all grade 1.

Figure 9:
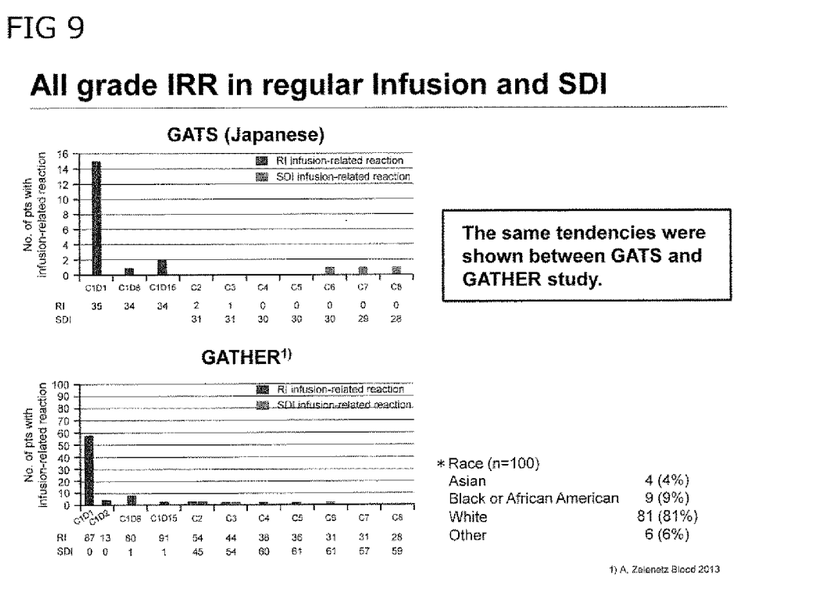
FIG. 9 shows number of patients with IRR in GATS and GATHER study. The same tendencies were shown between GATS and GATHER study. The same tendencies were shown between GATS and GATHER studies.

The observed rate of IRRs (49%) is concordant with other reports of obinutuzumab given by RI. Although this is not a direct comparison, it suggests that there is no increased risk of IRRs in patients treated with SDI obinutuzumab. In the phase III GALLIUM trial of obinutuzumab- vs. rituximab-based immunochemotherapy in 1202 previously untreated patients with FL, IRRs were the most common any-grade AEs (68% of obinutuzumab chemotherapy-treated patients) and grade ≥3 AEs (12% of obinutuzumab chemotherapy-treated patients) and typically occurred during the first infusion. Similarly, in the phase III GOYA study of 1418 patients with untreated DLBCL, IRRs occurred in 45% (any grade) and 10% (grade ≥3) of patients receiving obinutuzumab with CHOP. In the phase Ib GAUDI study, IRRs occurred in 18 of 28 patients (64%) receiving obinutuzumab plus CHOP; although this occurrence is more common than in the current study, IRRs were also mainly restricted to the first infusion, and grade 3-4 IRRs were infrequent, occurring in two patients (7%). IRRs have also predominated in studies in patients with B-cell malignancies in which obinutuzumab has been trialed as monotherapy, with the majority of reactions being grade 1 or 2. Notably, in the GATHER study in 100 mainly non-Asian patients with DLBCL who received obinutuzumab plus CHOP, no grade ≥3 IRRs were noted in patients who received SDI over 120 or 90 min. The pattern of IRRs seen in GATHER was similar to GATS, with most reactions (77%) occurring during Cycle 1 (during which RI was given) (FIG. 9). Other safety and tolerability findings were similar between the GATHER and GATS populations. No new safety signals were identified in the current study.

PK and serum cytokine data were also found to be comparable with the results of the GATHER study. Exposure to obinutuzumab after SDI was also of the same order in the current study as in GATHER, with similar $AUC_{0-7}$ and $t_{1/2}$ values. The $AUC_{last}$ value reported in the present study from Day 1 of Cycle 2 (4770±885 µg day/ml) is also of the same order of the $AUC_{last}$ reported by Ogura et al. on Day 8 of Cycle 1 in patients who received obinutuzumab 800 mg (4190±1190 µg day/ml) or 1200 mg (6540±1070 µg day/ml) in their dose-finding phase I study in 12 Japanese patients with relapsed or refractory B-cell NHL.

Patterns of inflammatory cytokine release, with rapid peaking during the first infusion followed by a rapid reduction and stabilization at baseline levels, were also similar to previous reports. The phase II GAUSS study in 175 patients with relapsed indolent B-cell NHL showed peak cytokine levels of IL6, IL8, IL10, TNFα and IFNγ that were notably elevated during the first infusion of obinutuzumab but then returned to baseline without any increase during subsequent infusions. The same pattern was reported in the phase I/II GAUGUIN study in the cohort of 33 patients with relapsed or refractory CLL. We note, as did the authors of GAUGUIN, that these early elevations in inflammatory cytokine levels coincide with the increased rates of reporting of IRRs during the first cycle of treatment in GATS and the other studies mentioned. The pattern of CD19-positive B-cell response was also similar to previous reports. Ogura et al. showed a rapid reduction after the first infusion of obinutuzumab, with the nadir achieved in most patients after infusion on Day 1. The same rapid Bcell depletion was reported in Cycle 1 of GAUGUIN in the CLL cohort and the indolent B-cell NHL cohort.

Overall and complete response rates at the end of treatment in patients with DLBCL (68 and 58%, respectively) were of the same order as those obtained in GATHER (82 and 55%, respectively), in which SDI was also used for patients with DLBCL. There are no data available yet for response rates in FL patients treated with obinutuzumab using SDI for comparison.

A limitation of the current study lies in the small patient population; a much larger sample would be required for definitive assessment of safety of obinutuzumab SDI, although the results obtained do appear concordant with previous findings in both Japanese patients and those undergoing treatment with SDI. We note also that the GATS study lacked a control arm in which, for example, patients might have received a conventional full set of cycles of obinutuzumab by RI in addition to CHOP.

Figure 14:
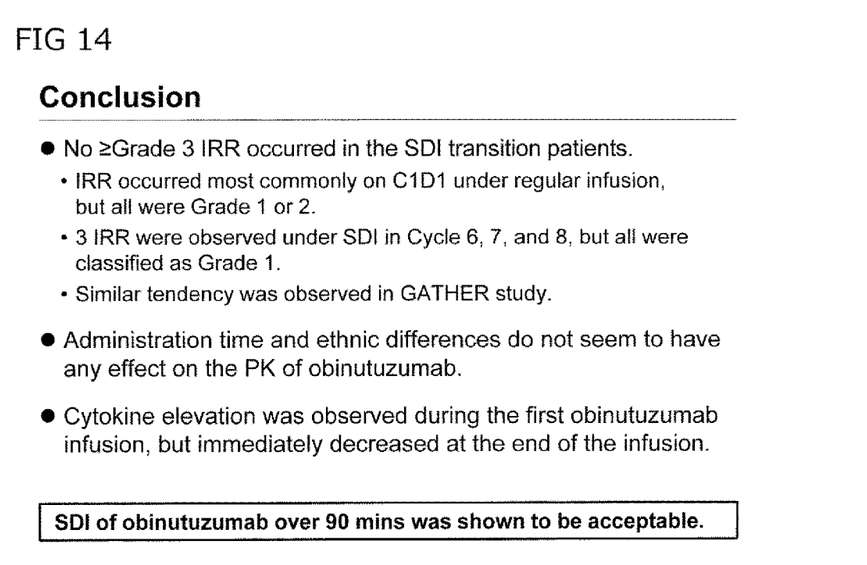
FIG. 14 shows acceptability for SDI of obinutuzumab on the basis of GATS study. No ≥Grade 3 IRR occurred in the SDI transition patients. IRR occurred most commonly on day 1 of cycle 1 under regular infusion, but all were Grade 1 or 2. 3 IRR were observed under SDI in cycle 6, 7, and 8, but all were classified as Grade 1. Similar tendency was observed in GATHER study. Administration time and ethnic differences do not seem to have any effect on the PK of obinutuzumab. Cytokine elevation was observed during the first obinutuzumab infusion, but immediately decreased at the end of the infusion. As a whole, SDI of obinutuzumab was shown to be acceptable.

In conclusion, obinutuzumab given by SDI was well tolerated in this Japanese patient cohort (FIG. 14). No SDI-associated IRRs were observed in the second cycle of treatment (i.e. the first SDI cycle); a small number of IRRs were observed with SDI in later cycles but were tolerable and manageable. The rate of IRRs was in line with findings from other studies of obinutuzumab given by RI, indicating that there is no increased risk of IRRs when obinutuzumab is given by SDI. Overall, the findings suggest that obinutuzumab can be administered safely by SDI.

The invention claimed is:

1. A method for treating a patient having a CD20-positive B-cell lymphoma, the method comprising administering to the patient a pharmaceutical composition comprising obinutuzumab by intravenous drip, wherein 1000 mg of obinutuzumab is infused per administration, and wherein the pharmaceutical composition is administered in at least a first cycle and a second cycle, wherein:

(a) in each infusion in the first cycle, (i) the obinutuzumab is administered at an initial administration speed of at least 50 mg of obinutuzumab an hour, and (ii) the administration speed is increased by 50 mg/hour every 30 minutes to a maximum administration speed of 400 mg of obinutuzumab per hour; and (b) the second cycle comprises a single infusion of obinutuzumab, wherein (i) the obinutuzumab is administered at an initial administration speed of 100 mg of obinutuzumab an hour for 30 minutes and (ii) the obinutuzumab is then administered at an administration speed of 900 mg of obinutuzumab per hour.

2. The method of claim 1, wherein the pharmaceutical composition is administered three times in the first cycle and once in the second cycle.

3. The method of claim 2, wherein a first administration in the first cycle is administered at an initial administration speed of 50 mg of obinutuzumab per hour, and a second or later administration in the first cycle is administered at an initial administration speed of 100 mg of obinutuzumab per hour.

4. The method of claim 2, wherein, in the second cycle, the patient has not experienced an infusion reaction of Grade 3 or above during the last three administrations and has a number of lymphocytes in peripheral blood of less than 5000 µL.

5. The method of claim 1, wherein the method further comprises decreasing the administration speed based on the condition of the patient.

6. The method of claim 1, wherein, in the second cycle, the patient experiences a Grade 1/2 infusion reaction, and the method further comprises stopping administration and restarting administration at half the administration speed before administration was stopped.

7. The method of claim 6, wherein the patient does not experience an infusion reaction within 30 minutes of restarting administration, and the method further comprises increasing the speed to 900 mg/hour.

8. The method of claim 1, wherein, in the second cycle, the patient experiences a Grade 3 infusion reaction, and the method further comprises stopping administration and restarting administration at an administration speed of 200 mg/hour or lower.

9. The method of claim 8, wherein the patient does not experience an infusion reaction within 30 minutes of restarting administration, and the method further comprises increasing the administration speed by 50 mg/hour every 30 minutes to a maximum of 400 mg/hour.

10. The method of claim 2, wherein the pharmaceutical composition is administered on days 1, 8 and 15 of the first cycle and on day 1 of the second cycle.

11. The method of claim 1, wherein the length of each cycle is three weeks.

12. The method of claim 1, wherein the pharmaceutical composition is administered in combination with at least one other anti-tumor agent, wherein the administration cycle of the pharmaceutical composition is synchronized with a dosing cycle of the at least one other anti-tumor agent, and wherein the length of the dosing cycle of the at least one other anti-tumor agent is four weeks.

13. The method of claim 12, wherein the at least one other anti-tumor agent is selected from cyclophosphamide, doxorubicin, vincristine, and prednisolone (CHOP); cyclophosphamide, vincristine, and prednisone (CVP); bendamustine; fludarabine; lenalidomide; an anti-PD-1 antibody; and an anti-PD-L1 antibody.

14. The method of claim 1, wherein, after the first cycle and second cycle, the pharmaceutical composition is administered every two months for two years as a maintenance monotherapy.

15. The method of claim 1, wherein the concentration of obinutuzumab in the infusion fluid is between 10 mg/ml and 40 mg/mL.

16. The method of claim 15, wherein the concentration of obinutuzumab in the infusion fluid is between 20 mg/ml and 30 mg/mL.

17. The method of claim 16, wherein the concentration of obinutuzumab in the infusion fluid is 25 mg/mL.

18. The method of claim 1, wherein the pharmaceutical composition further comprises a trehalose hydrate, L-histidine, L-histidine hydrochloride hydrate, or polyoxyethylene (160) polyoxypropylene (30) glycol as an additive.

19. The method of claim 1, wherein the CD20-positive B-cell lymphoma is a non-Hodgkin's lymphoma (NHL).

20. The method of claim 19, wherein the NHL is follicular lymphoma (FL), diffuse large B-cell lymphoma (DLBCL), or marginal zone lymphoma (MZL).

21. The method of claim 20, wherein the NHL is FL.

22. A method for treating a patient having follicular lymphoma (FL), the method comprising administering to the patient a pharmaceutical composition comprising obinutuzumab by intravenous drip, wherein 1000 mg of obinutuzumab is infused per administration, and wherein the pharmaceutical composition is administered in at least a first cycle and a second cycle, wherein:

(a) in each infusion in the first cycle, (i) the obinutuzumab is administered at an initial administration speed of at least 50 mg of obinutuzumab an hour, (ii) the administration speed is increased by 50 mg/hour every 30 minutes to an administration speed of 400 mg of obinutuzumab an hour, and (iii) the obinutuzumab is then administered continuously at an administration speed of 400 mg of obinutuzumab per hour; and (b) the second cycle comprises a single infusion of obinutuzumab, wherein (i) the obinutuzumab is administered at an initial administration speed of 100 mg of obinutuzumab an hour for 30 minutes and (ii) the obinutuzumab is then administered continuously at an administration speed of 900 mg of obinutuzumab per hour.

23. The method of claim 22, wherein a first administration in the first cycle is administered at an initial administration speed of 50 mg of obinutuzumab per hour, and wherein each of a second administration and a third administration in the first cycle is administered at an initial administration speed of 100 mg of obinutuzumab per hour.

24. The method of claim 23, wherein the length of each cycle is three weeks and the pharmaceutical composition is administered on days 1, 8 and 15 of the first cycle and on day 1 of the second cycle.

* * * * *

SEQUENCE LISTING

<160> NUMBER OF SEQ ID NOS: 2

<210> SEQ ID NO 1
<211> LENGTH: 449
<212> TYPE: PRT
<213> ORGANISM: Artificial Sequence
<220> FEATURE:
<223> OTHER INFORMATION: a heavy chain of obinutuzumab

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
              355                 360                 365
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 219
<212> TYPE: PRT
<213> ORGANISM: Artificial Sequence
<220> FEATURE:
<223> OTHER INFORMATION: a light chain of obinutuzumab

<400> SEQUENCE: 2

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

UNITED STATES PATENT AND TRADEMARK OFFICE
CERTIFICATE OF CORRECTION

| | | |
|---|---|---|
| PATENT NO. | : 12,129,304 B2 | Page 1 of 1 |
| APPLICATION NO. | : 16/756057 | |
| DATED | : October 29, 2024 | |
| INVENTOR(S) | : Michael Wenger et al. | |

It is certified that error appears in the above-identified patent and that said Letters Patent is hereby corrected as shown below:

In the Claims

Column 19, Lines 21-22, Claim 4, replace "5000µL" with --5000/µL--.

Column 20, Line 9, Claim 15, replace "10 mg/ml" with --10 mg/mL--;
    Line 12, Claim 16, replace "20 mg/ml" with --20 mg/mL--.

Signed and Sealed this
Sixth Day of May, 2025

Coke Morgan Stewart
*Acting Director of the United States Patent and Trademark Office*